(12) United States Patent
Coleman et al.

(10) Patent No.: US 7,647,846 B2
(45) Date of Patent: Jan. 19, 2010

(54) GAS SAMPLING APPARATUS

(76) Inventors: Dennis Coleman, Isotech Laboratories, 1308 Parkland Ct., Champaign, IL (US) 61820; Todd Coleman, Isotech Laboratories, 1308 Parkland Ct., Champaign, IL (US) 61820

( * ) Notice: Subject to any disclaimer, the term of this patent is extended or adjusted under 35 U.S.C. 154(b) by 0 days.

(21) Appl. No.: 10/257,514

(22) PCT Filed: Apr. 13, 2001

(86) PCT No.: PCT/US01/08652

§ 371 (c)(1),
(2), (4) Date: Apr. 2, 2003

(87) PCT Pub. No.: WO01/79805

PCT Pub. Date: Oct. 25, 2001

(65) Prior Publication Data

US 2004/0123679 A1    Jul. 1, 2004

Related U.S. Application Data

(60) Provisional application No. 60/197,181, filed on Apr. 14, 2000.

(51) Int. Cl.
*G01N 1/22* (2006.01)
(52) U.S. Cl. .................................................. 73/863.31
(58) Field of Classification Search . 73/863.31–863.33, 73/863.52, 863.71, 864.63, 864.67, 963.52
See application file for complete search history.

(56) References Cited

U.S. PATENT DOCUMENTS

| | | | |
|---|---|---|---|
| 2,298,627 A | | 10/1942 | Proudman et al. |
| 3,444,742 A | * | 5/1969 | Ellis et al. ................ 73/863.32 |
| 3,842,677 A | * | 10/1974 | Bufkin et al. ............ 73/863.31 |
| 4,470,316 A | * | 9/1984 | Jiskoot .................... 73/863.31 |
| 4,584,887 A | * | 4/1986 | Galen ...................... 73/863.31 |
| 4,712,434 A | | 12/1987 | Herwig et al. |

(Continued)

FOREIGN PATENT DOCUMENTS

WO    PCT/US04/38636 A1    5/2005

OTHER PUBLICATIONS

U.S. Appl. No. 10/578,973, filed Mar. 15, 2007, Coleman et al.

*Primary Examiner*—Hezron Williams
*Assistant Examiner*—Nashmiya S. Fayyaz

(57) ABSTRACT

The object of this invention is to provide a gas sampling system capable of taking discreet samples from a continuous flow of gas or fluid. Said apparatus offers a frame (1) and mounting components in the form of a fixed chuck (4) and a spring-loaded chuck with a sample container (5) mounted there between. The sampling container has self-sealing end cap valve assemblies (76) that automatically open when the sample container (5) communicates with the fixed chuck (4) and the spring loaded chuck (6) and the end cap valve assembly automatically closes when the sample container is removed. A value system allows the gas flow to be directed from one sample container to the other alternatively opening and closing a gas flow path. A sample extraction assembly (14) allows the efficient removal of samples from the sample containers. An extension rod pressurizer (117) in conjunction with the end cap value assembly, such as first end cap valve assembly (76) allow the sample to be pressurized to facilitate easy sample removal.

11 Claims, 12 Drawing Sheets

U.S. PATENT DOCUMENTS

| | | | |
|---|---|---|---|
| 4,800,763 A * | 1/1989 | Hakkers et al. | 73/863.31 |
| 5,031,469 A | 7/1991 | Blackburn et al. | |
| 5,116,330 A * | 5/1992 | Spencer | 73/863.71 |
| 5,131,282 A * | 7/1992 | Kuhner | 73/863.71 |
| 5,251,495 A | 10/1993 | Kuhner | |
| 5,341,692 A | 8/1994 | Sher et al. | |
| 5,361,643 A | 11/1994 | Boyd et al. | |
| 5,404,763 A * | 4/1995 | Guggenheim | 73/863.31 |
| 5,566,576 A | 10/1996 | Sher et al. | |
| 5,600,075 A | 2/1997 | Peterson | |
| 2004/0099068 A1 | 5/2004 | Welker | |
| 2004/0123679 A1 | 7/2004 | Coleman et al. | |

* cited by examiner

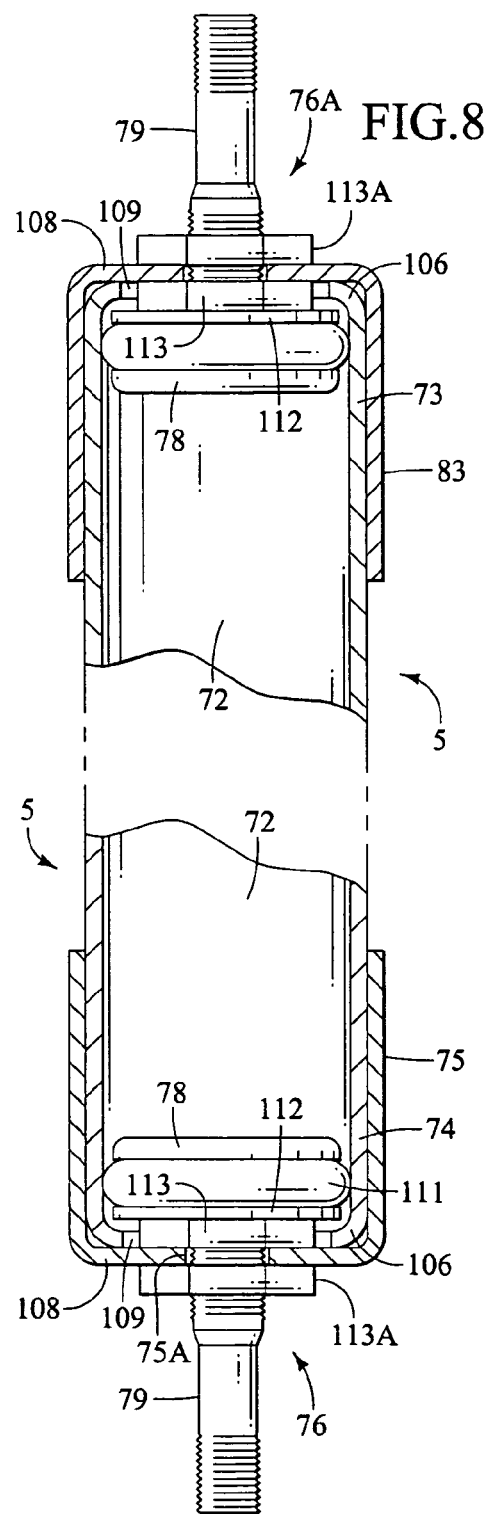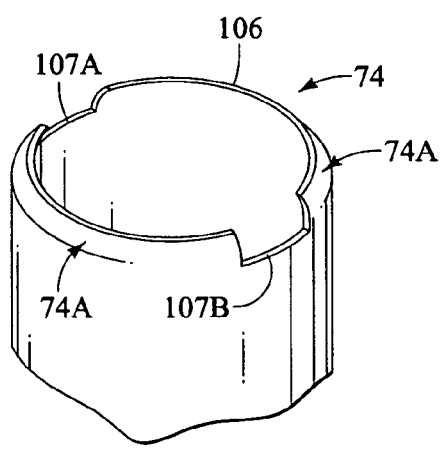
FIG.8
FIG.9

`US 7,647,846 B2`

GAS SAMPLING APPARATUS

CROSS REFERENCES TO RELATED APPLICATIONS

This Application claims the benefit of previously filed International Application PCT/US01/08652 which claims the benefit of previously filed U.S. Provisional Application Ser. No. 60/197,181, filed Apr. 14, 2000.

FEDERALLY SPONSERED RESEARCH

Not applicable.

SEQUENCE LISTING OR PROGRAM

Not applicable.

BACKGROUND OF THE INVENTION

1. Field of Invention

This apparatus relates to the collection, transportation and analysis of gas samples which may be required in various scientific, environmental and resource contests.

2. Background of the Invention

The oil and gas industry provides a suggested context in which to examine the need for collection, transportation and analysis of gas samples. In oil and natural gas exploration, drilling, recovery and storage, periodic sampling of recovered gases and fluid are required for subsequent analysis. In the oil industry, "mud" is a colloquial term for a thick chemical composition that is pumped into drills as they penetrate the substrate. This "mud" is returned to the surface and contains gases that are released from the rock as the drill penetrates. Significant data is acquired from the analysis of these gases. In the context of natural gas storage, large underground storage deposits are often chemically tagged for later identification. This apparatus facilitates the recovery of samples from these storage deposits for testing and identification of the chemical tag.

U.S. Pat. No. 5,116,330 to Spencer provided for a sample extraction system with a sampling container and valves. Such a sampling system requires the interruption of the fluid flow, as sampling containers are exchanged. Further, extraction of the sample from the sampling container was accomplished by "bleeding" the cylinder, a technique which relies on gravity and is suitable for fluids in a liquid rather than a gaseous state. Currently used in the industry are gas sample bags, which have the obvious problems of fragility, occupying a significant volume when being shipped and the inability to contain gas or fluid under any significant pressure.

OBJECTS AND ADVANTAGES

The present invention provides a gas sampling apparatus in which continuous or periodic gas samples may be isolated in gas sampling containers. The gas sampling container associated with this apparatus contains self-sealing valves on either end which open when the sample container is positioned in the apparatus and automatically closes when the sampling container is removed from the apparatus. In one configuration, the apparatus has two gas sampling tubes mounted and the gas flow which is to be sampled is directed into and out of one gas sampling container and then, by operating a valve system, the flow to be sampled can then be directed through a second sample container. Upon removal from the apparatus, the first sample container self-seals and may be transported. An empty container can then take its place. When the valve system again is actuated, the gas flow is re-directed from one sample container to the other. In this way, continuous sampling of a gas flow may be achieved. Further, mechanisms are provided that facilitate the pressurization and removal of gas samples from the sample containers.

This gas sampling apparatus can also find use in any industry in which the continuous sampling of flows of gases or fluids are required. Further, the assembly also has applicability in any industry in which gas samples need to be transported in either a pressurized or unpressurized state and later need to be easily removed from testing.

BRIEF DESCRIPTION OF THE DRAWINGS

FIG. 8 is a cross sectional view of the sampling container.

FIG. 9 is a perspective view of the sample container ends.

Figure 1:
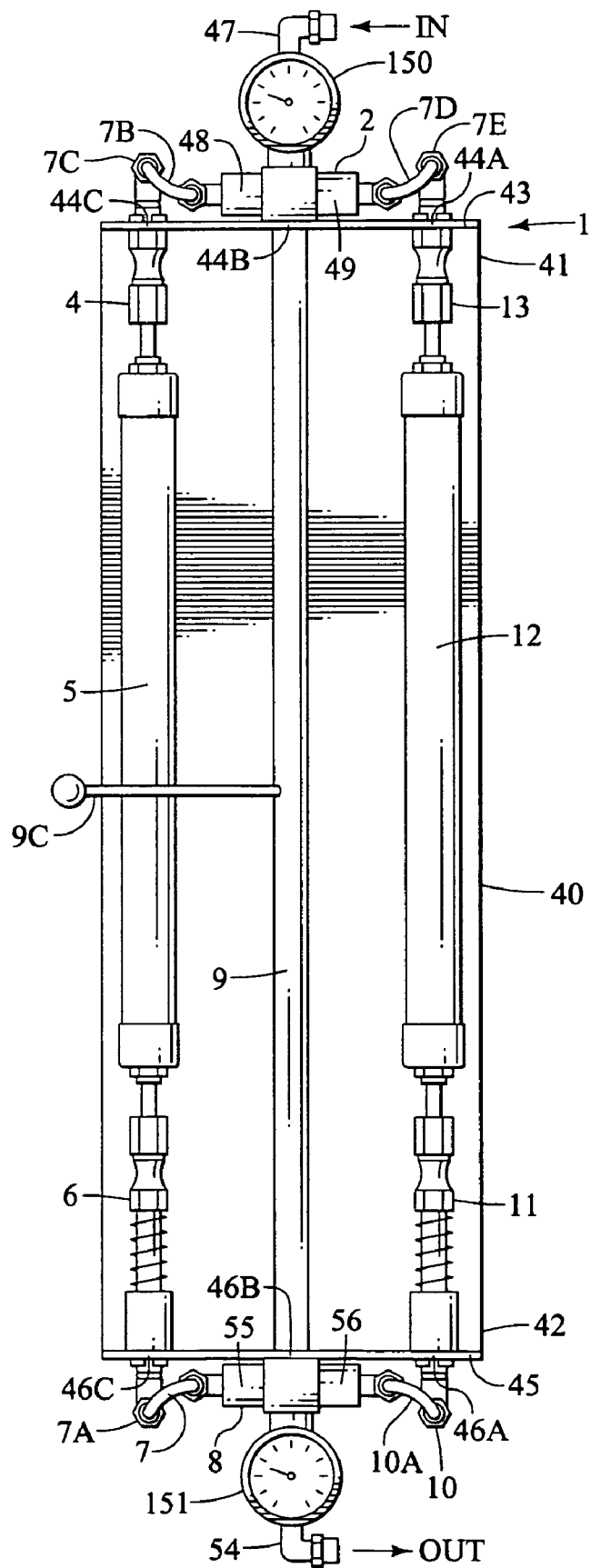
FIG. 1 is a front elevation view of the major components of the apparatus.

COMPONENT LISTING frame 1
first three-way valve 2
first fixed chuck 4
first sample container 5
first spring-loaded chuck 6
first flexible connector 7
first flexible connector fitting 7A
second flexible connector 7B
second flexible connector fitting 7C
third flexible connector 7D
third flexible connector fitting 7E
second three-way valve 8
valve control rod 9
first control rod end 9A
second control rod end 9B
control handle 9C
fourth flexible connector fitting 10
fourth flexible connector 10A
second spring loaded chuck 11
second sample container 12
second fixed chuck 13
sample extraction assembly 14
coupler 15 coupler body 15A
central longitudinal bore 15B
first body end 16
second body end 17
central bore 18
small diameter segment 19
first larger diameter segment 20
first lip 21
first largest diameter segment 22
second lip 23
second larger diameter segment 24
third lip 25
annular bushing 26
central bore 26A
bushing retaining cap 27
first seal 28
second seal 29
sample release device 30
stem 31
first stem end 32
second stem end 33
septum 34
septum seat 35
spring 35A
septum retaining cap 36
central conical aperture 36A
stem retaining screw 37
stem retaining screw central bore 37A
threaded portion 38
cap portion 39
longitudinal planar segment 40
first planar segment end 41
second planar segment end 42
first panel 43
first panel first aperture 44A
first panel second aperture 44B
first panel third aperture 44C
second panel 45
second panel first aperture 46A
second panel second aperture 46B
second panel third aperture 46C
first valve inlet 47
first valve left outlet 48
first valve right outlet 49
first valve flow director 50
passage 51
first passage end 52
second passage end 53
second valve outlet 54
second valve left inlet 55
second valve right inlet 56
second valve flow directing means 57
conduit 58
first conduit end 59
second conduit end 60
annular body 61
internally threaded end 62
externally threaded end 63
first central bore section 64
second central bore section 64A
central bore 65
seat 66
plunger depressor 67
first finger member 68
first transverse member 69
air passage aperture 70
first flexible washer 71 first flexible washer central bore 71A
first annular chamber 72
second annular chamber end 73
first annular chamber end 74
edge tabs 74A
first end cap 75
first end cap central bore 75A
first self sealing valve 76
second self sealing valve 76A
first end cap valve body 77
transverse base 78
annular section 79
first annular section end 80
internal threads 80A
external threads 80B
second externally threaded annular section end 81
central bore valve seat section 82
second end cap 83
first plunger-activated valve 86
valve body 86A
plunger 87
plunger gasket 88
spring 89
central cavity 90
first plunger valve body end 91
central bore 92
first valve body aperture 93A
second valve body aperture 93B
second plunger valve body end 94
first plunger rod support 96
interior surface 96A
first plunger rod support aperture 98A
second plunger rod support aperture 98B
second plunger rod support 99
second plunger rod support first aperture 101A
second plunger rod support second aperture 101B
annular space 102
first plunger end 103
cap 103A
second plunger end 104
cap 104A
conical plunger valve body segment 105
first swaged edge 106
first opposite notch 107A
second opposite notch 107B
end cap exterior 108
first annular chamber end central aperture 109A
first end cap central aperture 109
valve body central bore 110
annular rubber ring 111
washer 112
nut 113
cap retaining nut 113A
plunger valve body gasket 114
spring stop 115
a first plunger depressor retaining cap 116
first chuck head 117
extension rod pressurizer 117A
first pipe 118
first pipe first end 118A
first pipe second end 118B
snap ring 118C
spring 118D
bolt 119
tube 119A
lock nut 120
first bushing 121 first swage 121A
second swage 121B
third swage 121C
fourth swage 121D
plunger depressor 123
finger member 124
transverse member 125
stem member 126
spring 127
seat 128
seal 129
sample container 130
central bore 130A
first internally threaded end 131
second internally threaded end 132
first externally threaded end valve 133
second externally threaded end valve 133A
first pressure gauge 150
second pressure gauge 151

DETAILED DESCRIPTION OF THE INVENTION

FIG. 1. illustrates the major components of the gas sampling apparatus. The gas sampling apparatus is given structure by its frame 1. The frame is composed of a rigid substance, usually metal, and exhibits a longitudinal planar segment 40. The frame is further composed of a first planar segment end 41 and a second planar segment end 42. A first panel 43 emanates from the first planar segment end 41 and is oriented at right angles to the planar segment 40. The first panel 43 exhibits a plurality of apertures first panel first aperture 44A, first panel second aperture 44B and first panel third aperture 44C. A second panel 45 emanates from the second planar segment end 42 again at right angles to the planar segment 40. The second panel 45 also exhibits a plurality of apertures, second panel first aperture 46A, second panel second aperture 46B and second panel third aperture 46C, in this case three in number, that correspond to and are opposite the apertures 44A, 44B and 44C, exhibited by first panel 43. Mounted to first panel 43 and through the outermost apertures 44A and 44C of first panel 43 are first fixed chuck 4 and second fixed chuck 13. Mounted to second panel 45 and within the outermost apertures 46A and 46C are first spring-loaded chuck 6 and second spring loaded chuck 11.

Figure 16:
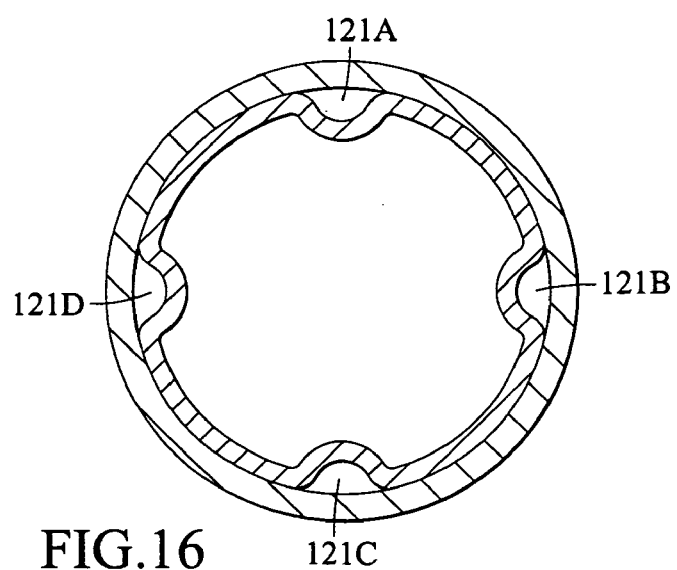
FIG. 16 is a view of an alternative mechanism assuaging the ends of the sampling container.

First spring-loaded chuck 6 and second spring-loaded chuck 11 as well as first fixed chuck 4 and second fixed chuck 13 their associated flexible connectors and the frame provide the mounting apparatus for first sample container 5 and the substantially similar, second sample container 12. Turning for a moment to FIG. 8, it is seen that the first sample container 5 is composed of a first annular chamber 72 exhibiting a first annular chamber end 74 and a second annular chamber end 73. FIG. 9 shows that first annular chamber end 74 exhibits first swaged edge 106 with first opposite notch 107A and second opposite notch 107B. Turning to FIG. 16, and alternative means of swaging the edge is seen. Here the edge is swaged in a plurality of small increments or dimples, first swage 121A, second swage 121B, third swage 121C and fourth swage 121D, around the edge's diameter. This can facilitate the insertion of other forms of end cap valves. Turning now to FIG. 8, the first swaged edge 106 of first sample container 5 is shown disposed within the first end cap central bore 75A of first end cap 75. Disposed through both first annular chamber end central aperture 109A and first end cap central aperture 109 is first self-sealing valve 76. The end caps and nuts fixing the end caps to the self-sealing valves constitute the self-sealing valve.

Figure 12:
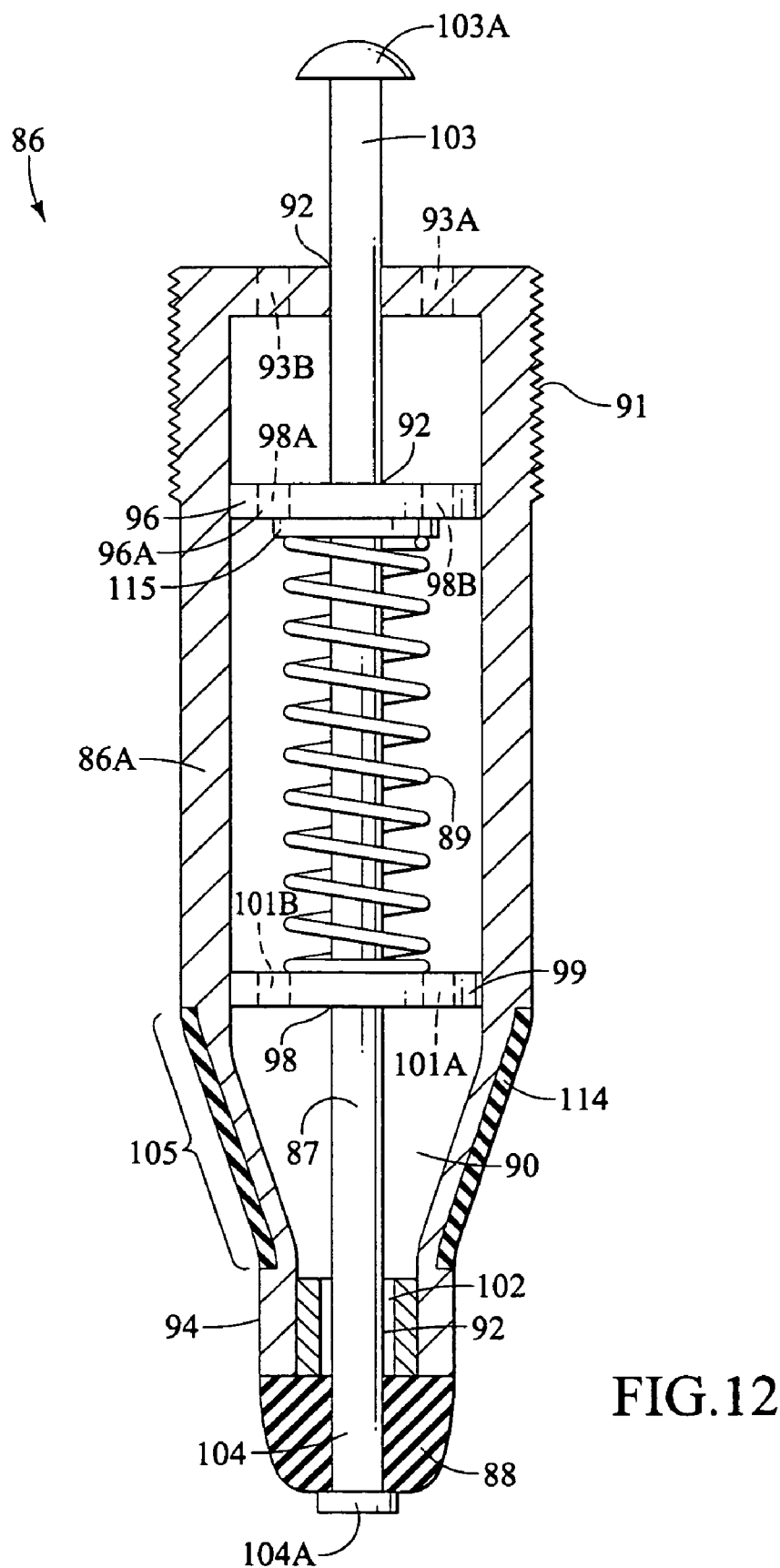
FIG. 12 is a cross sectional view of the plunger-activated valve.
Figure 15:
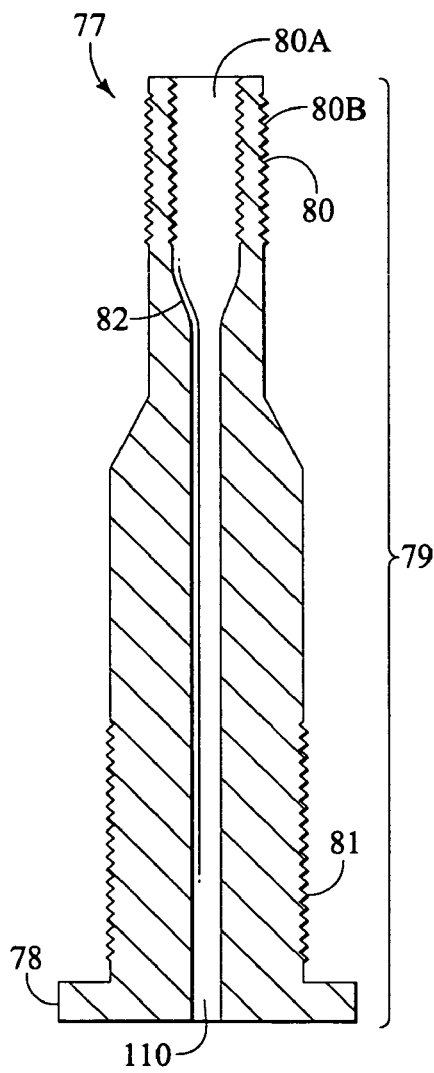
FIG. 15 is a cross sectional view of the first end cap valve body.

Turning now to FIG. 15, the first end cap valve body 77 is illustrated which is one of the components of the first end cap valve assembly 76. It is composed of a transverse base 78 and annular section 79. Annular section 79 exhibits first annular section end 80 and second externally threaded annular section end 81, which is attached to the transverse base 78. Valve body central bore 110 extends through both transverse base 78 and the annular section 79. The first annular section end 80 exhibits both external threads 80B and internal threads 80A within the valve body central bore 110. The valve body central bore 110 exhibits a conical narrowing that comprises the central bore valve seat section 82. It is here that a first plunger-activated valve 86 as seen in FIG. 12, is seated. Turning now to FIG. 12, plunger activated valve 86 is shown. First plunger activated valve 86 is composed of a valve body 86A having a central cavity 90. Externally threaded first plunger valve body end 91 has a central bore 92 and a plurality of apertures, first valve body aperture 93A and second valve body aperture 93B that communicate with the central cavity 90. The second plunger valve body end 94 also exhibits a corresponding central bore 95 with an annular space 102 also communicating with the central cavity 90. The exterior of the valve body 86 exhibits a conical plunger valve body segment 105. A plunger valve body gasket 114 is seated around the conical plunger valve body segment 105 and substantially corresponds to the shape of the central bore valve seat section 82 shown in FIG. 15. Within the central cavity 90, first plunger rod support 96 has a central bore 92 and a plurality of plunger rod support apertures, first plunger rod support aperture 98A and second plunger rod support aperture 98B. The first plunger rod support is fixed to the interior walls of the central cavity 90. A second plunger rod support 99 also has a central bore 92 and a plurality of apertures second plunger rod support first aperture 101A and second plunger rod support second aperture 101B. The second plunger rod support 99 is also fixed to the interior walls of the central cavity 90. Thus, the central bores of the second plunger valve body end 94, the second plunger rod support 99, the first plunger rod support 96 and the first plunger valve body end 91 all correspond such that plunger 87 can be disposed through all. Plunger 87 has a first plunger end 103 disposed outside central cavity 90 and above valve body 86A. First plunger end 103 also exhibits a cap 103A that acts as a stop and prevents first plunger end 103 from fully entering valve body 86A. A second plunger end 104 is also disposed outside the central cavity 90 and below valve body 86. Second plunger end 104 exhibits cap 104A which prevents the second plunger end 104 from fully entering valve body 86A and also provides an air tight seal against plunger gasket 88. Plunger 87 also exhibits spring stop 115 fixed to plunger 87 between first plunger rod support 96 and second plunger rod support 99 but at a point on plunger 87 where the spring stop 115 communicates with the interior surface 96A of the first plunger rod support 96 when in a resting position. The resting position is maintained by spring 89 disposed over the plunger rod and communicating with spring stop 115 in the second plunger rod support 99. Fixed to the second plunger end 94 in such a manner as to preclude leakage around the plunger 87 is plunger gasket 88. Plunger gasket 88 seals the central bore 95 and annular space 102 of second plunger valve body end 94 by being held against the second plunger valve body end 94 by the pressure exerted by spring 89 on spring stop 115. Now returning to FIG. 15, it can be seen that when second plunger valve body end 94 of plunger activated valve 86 is inserted into first annular section end 80 of first end cap valve body 77, externally threaded first plunger valve body end 91 may be disposed and threadedly mounted within the internal threads 80A of first annular section end 80. Disposition of plunger activated valve 86 is to such a depth as to press plunger valve body gasket 114 (FIG. 12) firmly against central bore valve seat section 82 creating a seal.

Turning again to FIG. 8, it is seen that an annular rubber ring 111 is disposed over the annular section 79 and seats on the transverse base 78. Washer 112 is likewise disposed over the annular section 79 and seats on the annular rubber ring 111. Nut 113 is then threaded down over the second externally threaded annular section end 81 seen in FIG. 15. Insertion of the components of the first end cap valve stem assembly is facilitated by first opposite notch 107A and second opposite notch 107B shown in FIG. 9. Edge tabs 74A are those areas of the wall curved inward between the opposing notches. Once the first self sealing valve 76 is within the first annular chamber 72, nut 113 is tightened thereby applying pressure to washer 112 which in turn applies pressure to and expands the annular rubber ring 111 such that full diameter contact with the walls of the first annular chamber 72 and a tight seal is achieved. The first end cap 75 is then disposed over the first annular chamber end 74. Cap retaining nut 113A is then disposed over annular section 79 and then threaded over second annular section end 81 until the nut communicates with the end cap exterior 108. The first self sealing valve 76 is then drawn toward the first swaged edge 106 which now retains the end cap valve assembly within first annular chamber 72 and holds the end cap in place. The second end cap 83 and second self sealing valve 76A are similarly mounted within the second annular chamber end 73.

Figure 6:
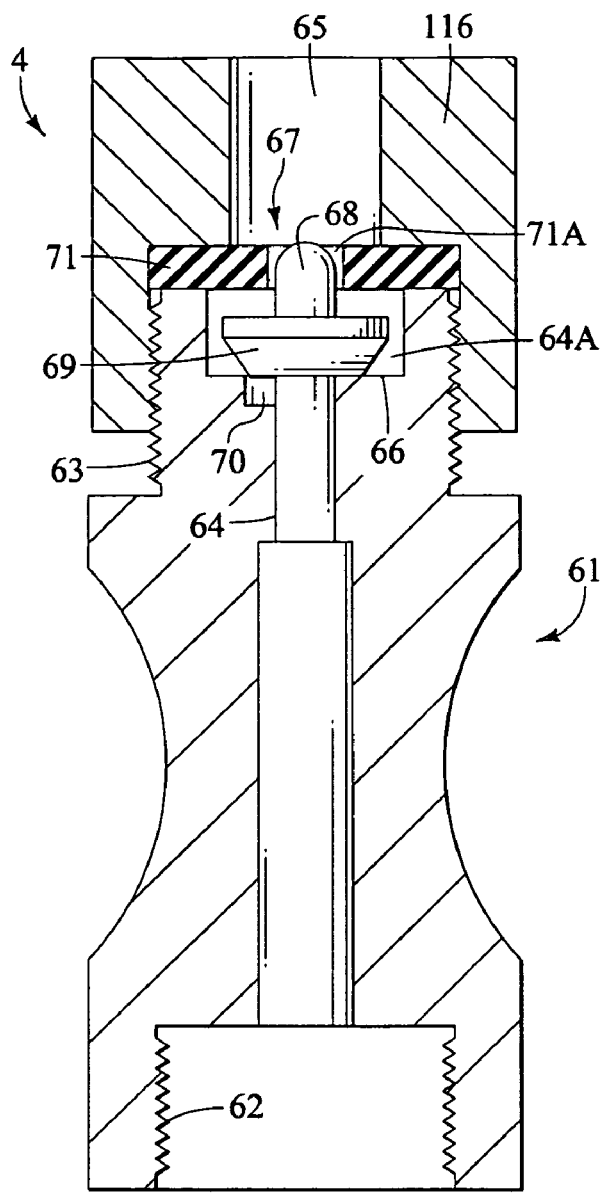
FIG. 6 is a cross sectional view of a fixed chuck.
Figure 7:
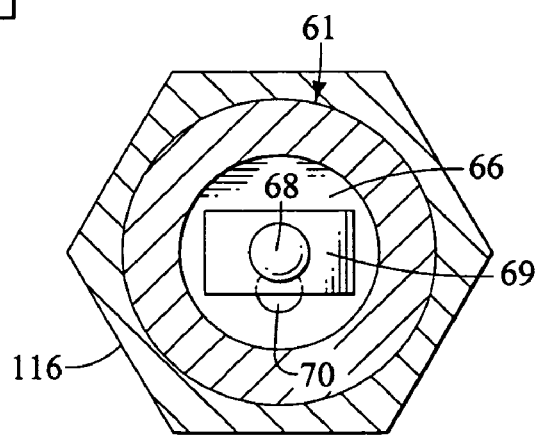
FIG. 7 is a plan view of the top of the fixed chuck.

Now turning to FIG. 6, first fixed chuck 4 is illustrated. First fixed chuck 4 is composed of an annular body 61 with externally threaded end 63 and internally threaded end 62. A central bore exists between them. A first central bore section 64 is seen followed by larger diameter second central bore section 64A. The differences in diameters produce seat 66. Upon seat 66 rests plunger depressor 67. Plunger depressor 67 has two components, a first finger member 68 and a first transverse member 69. The first transverse member 69 is that portion of the plunger depressor 67 which communicates with the seat 66. A first flexible washer 71 is disposed over the first finger member 68, first finger member disposed within first flexible washer central bore 71A, such that first flexible washer 71 rests on externally threaded end 63. However, as shown in FIG. 7, the first transverse member is not a disk but is rectangular in shape such that only a portion of first flexible washer 71 is in contact with first transverse member 69 thus allowing fluid or gas to flow through first flexible washer 71, past first transverse member 69 into air passage aperture 70 and then into first central bore section 64 and beyond. FIG. 6 shows a first plunger depressor retaining cap 116 which is disposed over the externally threaded end 63. It holds first flexible washer 71 in position and thereby retains plunger depressor 67. First plunger depressor retaining cap 116 exhibits a central bore 65 into which a first endcap valve assembly 76 or second endcap valve assembly 76A can be inserted. The second fixed chuck 13 is configured substantially similar to the first fixed chuck 4.

Figure 10:
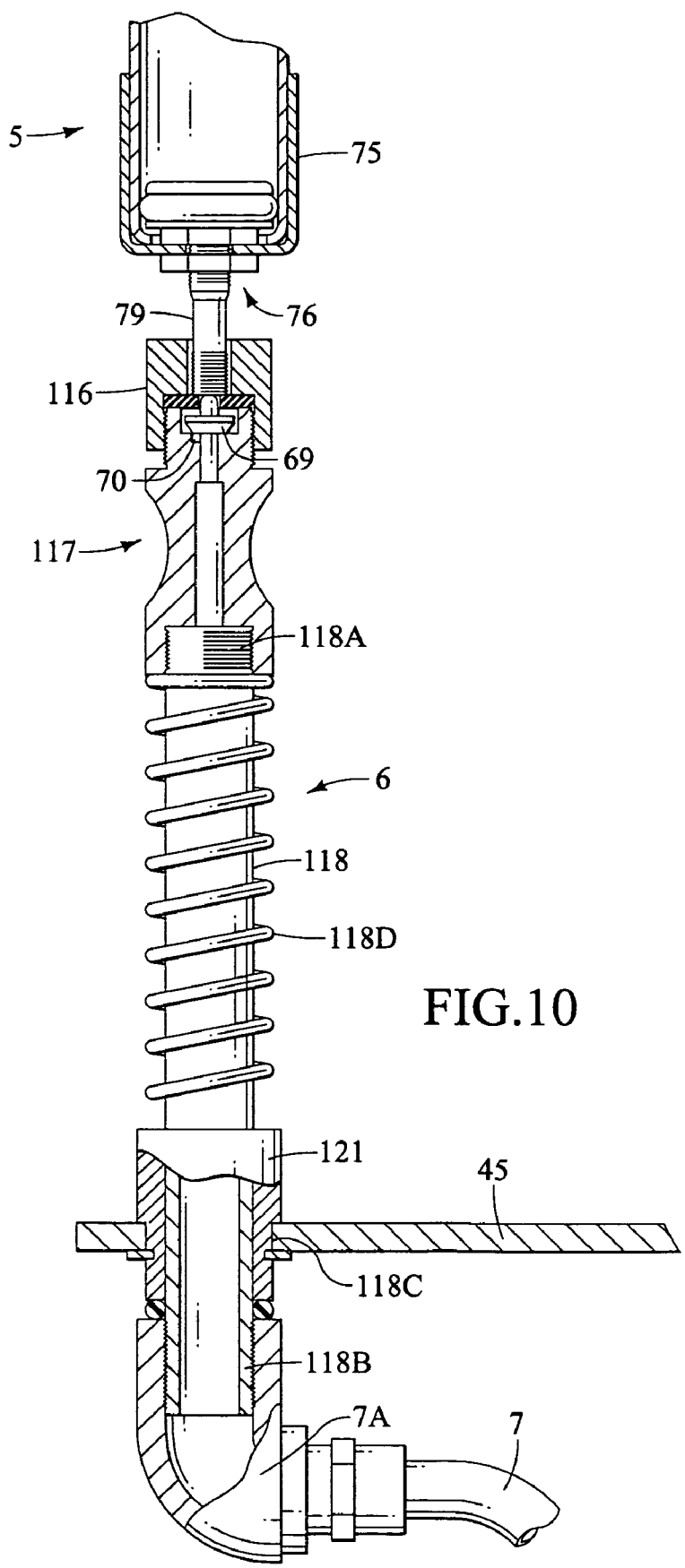
FIG. 10 is a cross sectional view of the spring-loaded chuck with the sample container seated therein.
Figure 11:
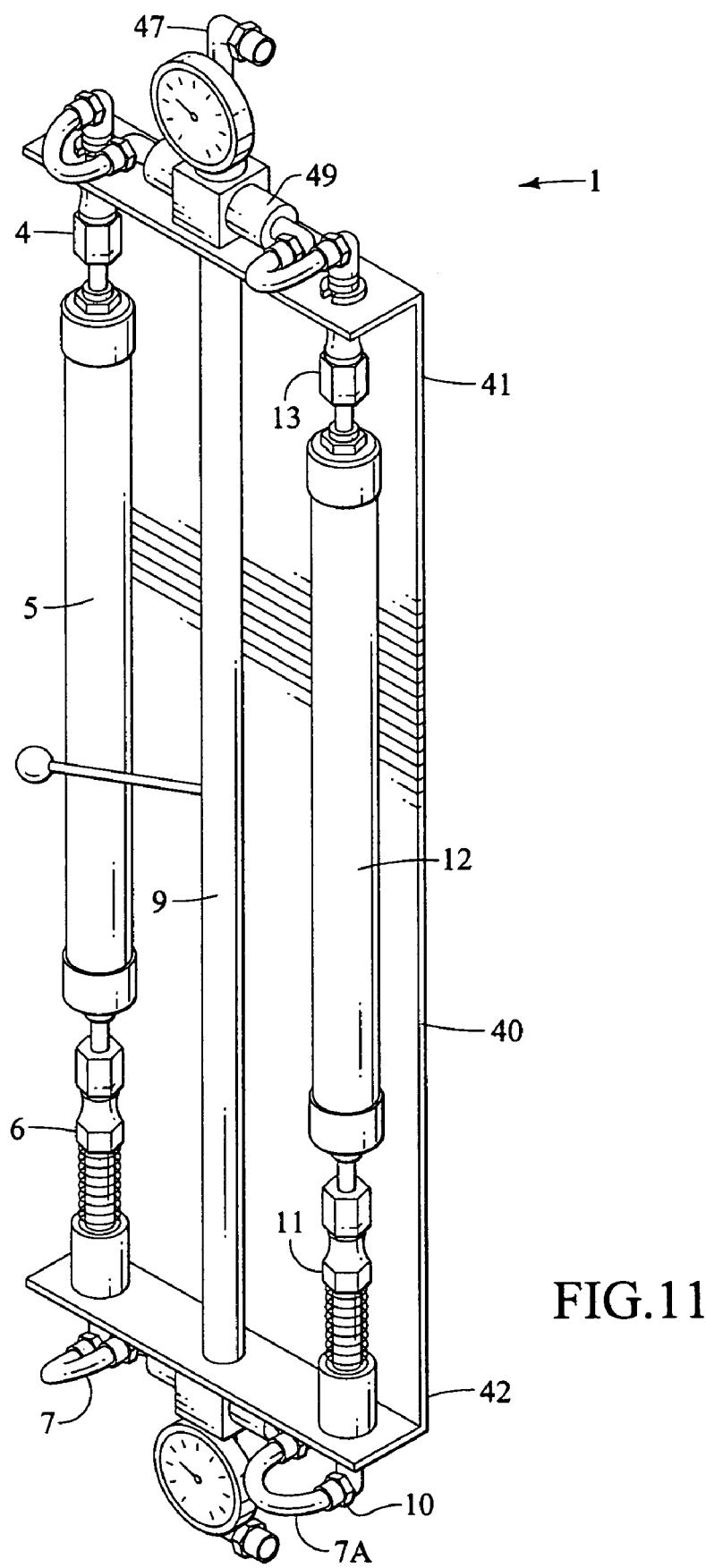
FIG. 11 is a perspective view of the apparatus.

Configured similarly to the fixed chucks 4 and 13 is the first chuck head 117 of the first spring loaded chuck 6 and second spring loaded chuck 11 as shown in FIG. 10. Disposed within the internally threaded end of first chuck head 117 is first pipe 118 having first pipe first end 118A and first pipe second end 118B. First pipe 118 then extends through first bushing 121 with first pipe second end 118B threadedly attached to a first flexible connector fitting 7A of such a diameter as to prevent pipe 118 from being returned through bushing 121. Bushing 121 is fixed within an outer second panel aperture 46C of second panel 45 by snap ring 118C. Spring 118D is disposed over pipe 118 and rests between chuck head 117 and bushing 121. When chuck head 117 is depressed by sample container 5, pipe 118 slides downward through bushing 121. As chuck head 117 is depressed, the tension in spring 118D is increased allowing chuck head 117 to return upward after pressure is released. Second spring loaded chuck 11 is configured in a substantially similar fashion being mounted in the second panel first aperture 46A of panel 45.

It can be seen in FIG. 1 that to insert a sample container, for example, sample container 5, the second self sealing valve 76A is disposed within the mouth of spring loaded chuck 6. Downward pressure is then applied whereupon first spring loaded chuck 6 is pressed down and through spring loaded chuck first bushing 121. Spring loaded chuck 6 is able to be depressed a sufficient distance to allow the upper end of sample container 5 to be positioned under fixed chuck 4. Downward pressure on the sample container is then released allowing the first self sealing valve 76 of sample container 5 to seat within fixed chuck 4. A similar procedure is utilized to mount the second sample container 12 between the second spring loaded chuck 11 and second fixed chuck 13.

At this point, it should be noted that the insertion of the end cap valve assemblies into spring loaded chuck 6 and fixed chuck 4 causes the ends of the end cap valve assemblies to be pressed into and to be pressed against the flexible washers such as the first flexible washer 71 as illustrated in FIG. 10. This produces a seal. A finger member such as first finger member 68 of plunger depressor 67 will come in contact with a plunger such as plunger 87 of plunger activated valve 86, (Seen in FIG. 12) causing the sample container, such as sample container 5 to open. This happens on both ends of the sample container allowing gas or fluid to pass through when the sample container is seated in the fixed and spring loaded chucks.

Returning to FIG. 1, first three-way valve 2 is mounted to panel 43 between first fixed chuck 4 and second fixed chuck 13. First fixed chuck 4 is connected to the first valve left outlet 48. The second fixed chuck 13 is connected to the first valve right outlet 49. Mounted so as to read pressure from the first valve inlet 47 is pressure gauge 150. A similar configuration is seen with the second three-way valve 8, which is similarly attached to second panel 45. The first spring loaded chuck 6 is connected to the second valve left inlet 55. Second spring loaded chuck 11 is further connected to second valve right inlet 56. Mounted to communicate and to read pressure from second valve outlet 54 is second pressure gauge 151. Since first spring loaded chuck first pipe 118 may be pressed through first spring loaded chuck first bushing 121, the first spring loaded chuck 6 is connected to second valve left inlet 55 by means of first flexible connector 7. Similarly, second spring loaded chuck 11 is connected to second valve right inlet 56 by means of second flexible connector 10. Valve control rod 9 extends through the second panel aperture 46B in second panel 45 and first panel aperture 44B in first panel 43. Thus control rod 9 communicates simultaneously with first three-way valve 2 and second three-way valve 8. Control handle 9C communicates with control rod 9 facilitating its rotation. The first three way valve, second three way valve, control rod and control handle comprise the flow director.

Figure 2:
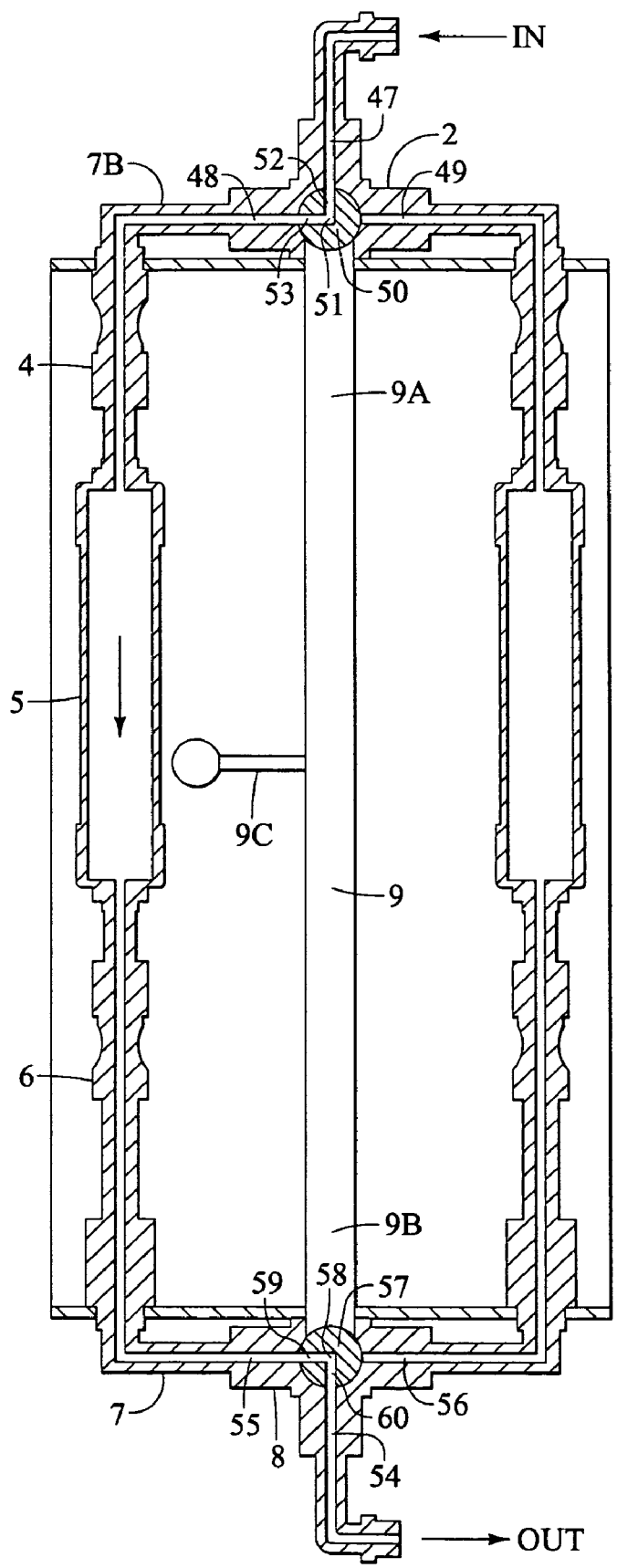
FIG. 2 is a cross sectional diagram of the flow of gas or fluid through the left half of the system.
Figure 3:
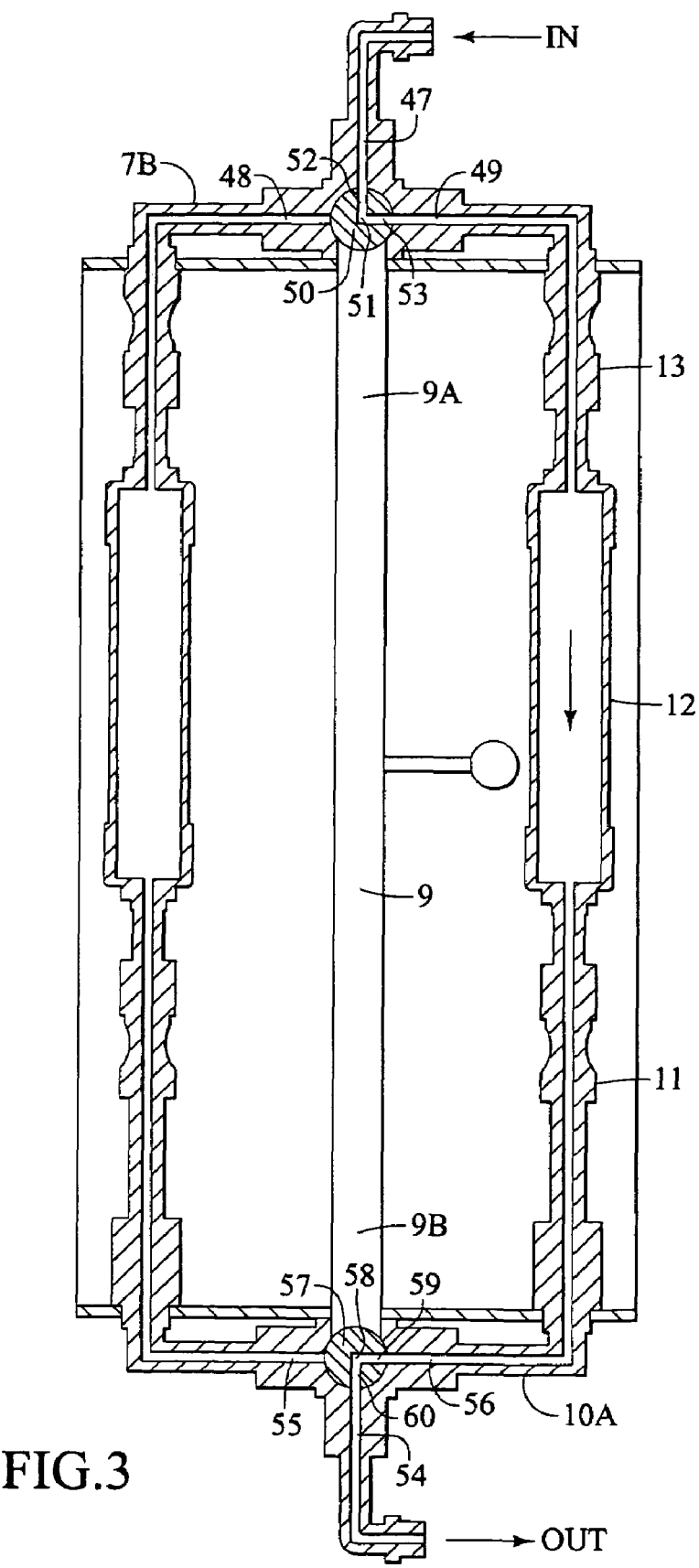
FIG. 3 is a cross sectional view of the gas flow through the right half of the system.

Now turning to FIG. 2, we first see that control handle 9C is oriented toward first sample container 5. Control rod 9 exhibits first control rod end 9A and second control rod end 9B. First control handle end 9A is attached to and operates a first valve flow director 50 which is mounted internally in first three-way valve 2. The first valve flow director 50 exhibits a passage 51 with a first passage end 52 and a second passage end 53. When the control handle 9A is orientated toward sample container 5, first passage end 52 aligns with first valve inlet 47. Simultaneously, the second passage end 53 aligns with first valve left outlet 48. It can then be seen that gas may flow into the first valve inlet 47 through first valve flow directing means passage 51, out first valve left outlet 48, through second flexible connector 7C, then through first fixed chuck 4 into sample container 5. Control rod second end 9B is similarly connected to second valve flow directing means 57. The second valve flow directing means exhibits conduit 58 which provides the same function as passage 51 in first valve flow directing means 50. Conduit 58 exhibits a first conduit end 59 and second conduit end 60. Control rod 9 is attached to both the first valve flow directing means 50 and second valve flow directing means 57 such that when the first valve flow directing means 50 is oriented as described above, the second valve flow directing means 57 is oriented in such a way that first conduit end 59 communicates with second valve inlet 55 and second conduit end 60 communicates with second valve outlet 54. It can be seen that any gas or fluid in sample container 5 may then flow through second spring loaded chuck 6 through first flexible connector 7 into second valve left inlet 55 through the second valve flow director conduit 58 and finally out second valve outlet 54. In this configuration, no gas will flow through first valve right outlet 49, through second sample container 12 or second valve right inlet 56. Now turning to FIG. 3, it can be seen that when control handle 9C is directed toward second sample container 12, the first valve flow directing means 50 is oriented such that first passage end 52 communicates with first valve inlet 47 and second passage end 53 is now oriented with first valve right outlet 49. Now it can be seen that gas may flow in first valve inlet 47 through first valve flow directing means passage 51 into the first valve right outlet 49 through fixed chuck 13 and into second sample container 12.

Again, when control handle 9C is oriented towards second sample container 12, the second valve flow directing means 57 has its conduit 58 oriented in such a way that first conduit end 59 communicates with second valve inlet 56 and second conduit end 60 communicates with second valve right outlet 54. Now it can be seen that fluid or gas in sample container 12 may flow through spring loaded chuck 11 then through second flexible connector 7B into second valve inlet 56 through conduit 58 and into second valve outlet 54.

A method of acquiring samples would be to allow gas to flow though sample container 5 and then after having mounted sample container 12, orienting the control handle so that gas now flows through sample container 12 and gas flow is terminated through sample container 5. In this way, sample container 5 may be removed from the system and an empty sample container mounted. When sufficient sample has been gathered within sample container 12, the control handle 9C would then again be moved toward the fresh sample container thus occluding gas flow through sample container 12 whereupon it may be removed from the system. By alternating the removal of full sample containers and the replacement with empty containers, continuous or periodic samples in a line of gas or fluid flow may be obtained.

Figure 4:
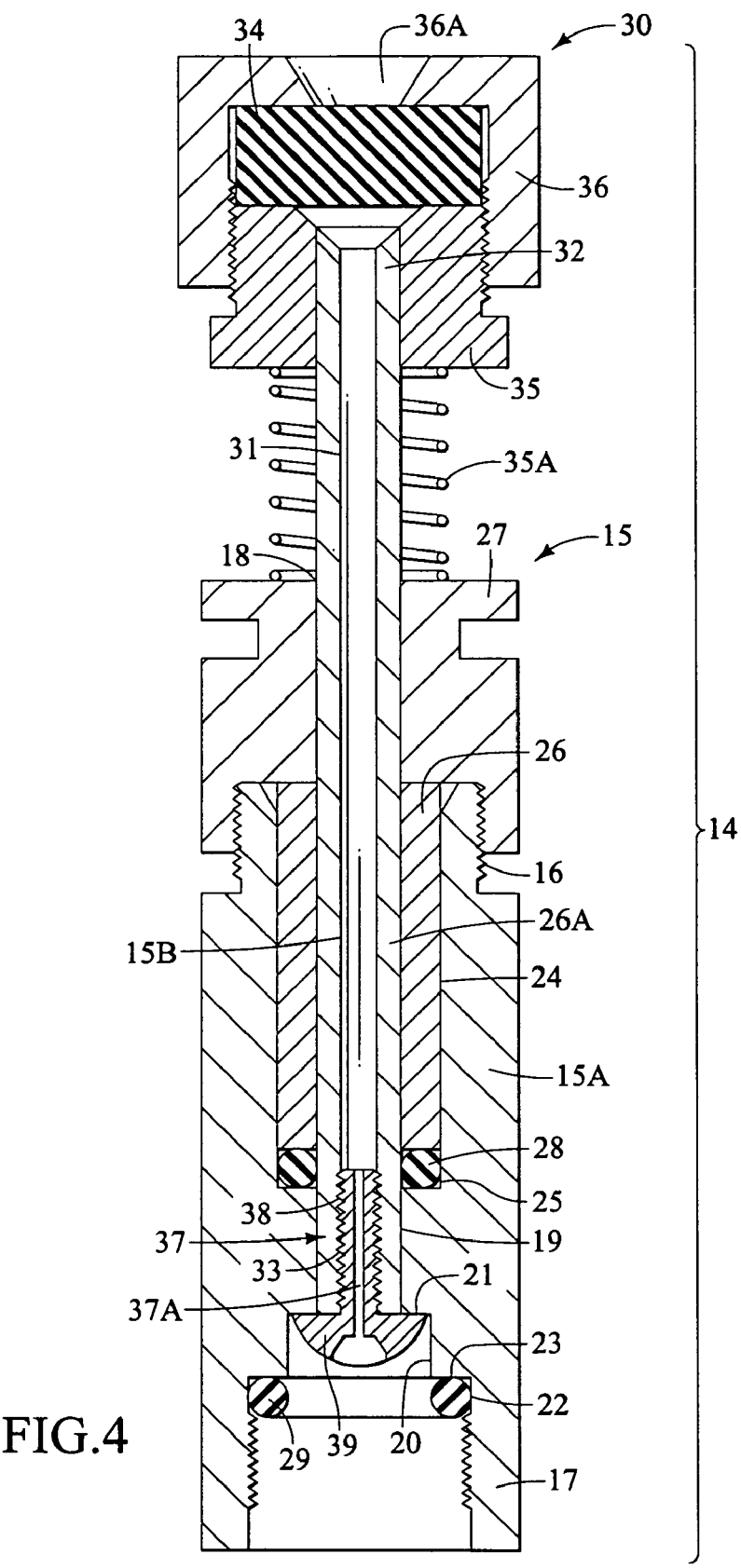
FIG. 4 is a cross sectional view of the sample extraction assembly.

Once the sample container is removed from the gas sampling apparatus the fluid or gas sample must be removed from the container. FIG. 4 illustrates the sample extraction assembly 14. It is composed of a coupler 15. Coupler 15 exhibits a coupler body 15A. The coupler body has a central longitudinal bore 15B which allows for fluid flow. The coupler also has an externally threaded first body end 16 and an internally threaded second body end 17. The central longitudinal bore 15 B is divided into segments of varying diameters. The narrowest diameter is the small diameter segment 19. Immediately below, is the first larger diameter segment 20. The differences in diameter allow the formation of first lip 21. Again below, toward the internally threaded second body end 17 is the first largest diameter segment 22. The differences in diameter again allow the formation of another lip, second lip 23. Upon second lip 23 rests a second seal 29 usually in the form of a rubber o-ring. This allows the internally threaded second body end 17 to be disposed over the externally threaded end of a first annular section end 80 of an end cap valve assembly such as first self sealing valve 76 thus creating a seal for gas or fluid. Returning to the description of the central longitudinal bore 15B, we now have a second larger diameter segment 24 above, toward the externally threaded first body end 16. The difference in diameter between the small diameter segment 19 and a second larger diameter segment 24 creates a third lip 25. Disposed within the second larger diameter segment 24 and resting on the third lip 25 is first seal 28, again seen usually in the form of a rubber o-ring. Annular bushing 26 exhibiting a central bore 26A communicates with the walls of the second larger diameter segment 24 and is coterminous with the externally threaded first body end 16. An internally threaded bushing retaining cap 27 having a central bore, is disposed over the externally threaded first body end 16. The sample release device 30 exhibits stem 31 which is partially disposed within the central bore 18 of bushing retaining cap 27, the central bore of the annular bushing 26 and the small diameter segment 19 and may slide within. First seal 28 communicates with stem 31 thereby preventing the passage of fluid or gas around the stem. Stem 31 has a first stem end 32 and an internally threaded second stem end 33. Mounted within the internally threaded second stem end 33 is externally threaded stem retaining screw 37 having a threaded portion 38 and a cap portion 39. The cap portion 39 is of a larger diameter than stem 31 and thereby is able to rest on first lip 21. The stem retaining screw 37 thus secures stem 31 within body 15A. The stem retaining screw 37 also exhibits a central bore that communicates with the central bore of stem 31. First stem end 32 is attached to externally threaded septum seat 35. Septum 34 rests on said septum seat 35 and is composed of a penetrable material such as rubber. Septum 34 is held in place by internally threaded septum retaining cap 36. A spring 35A is located between the septum seat 35 and internally threaded bushing retaining cap 27 which is disposed over externally threaded first body end 16.

After the sample extraction assembly 14 is threadedly attached to an end cap valve assembly, such as first self sealing valve 76, a needle such as a hypodermic needle, is inserted through the central conical aperture 36A of the septum retaining cap 36. Depressing the sample release device 30 compresses spring 35A. In turn, stem 31 and stem retaining screw 37 are depressed such that stem retaining screw makes contact with plunger 87 shown in FIG. 12 thereby opening the sample container, such as sample container 5. When this is accomplished the sample may be extracted from the container.

Figure 13:
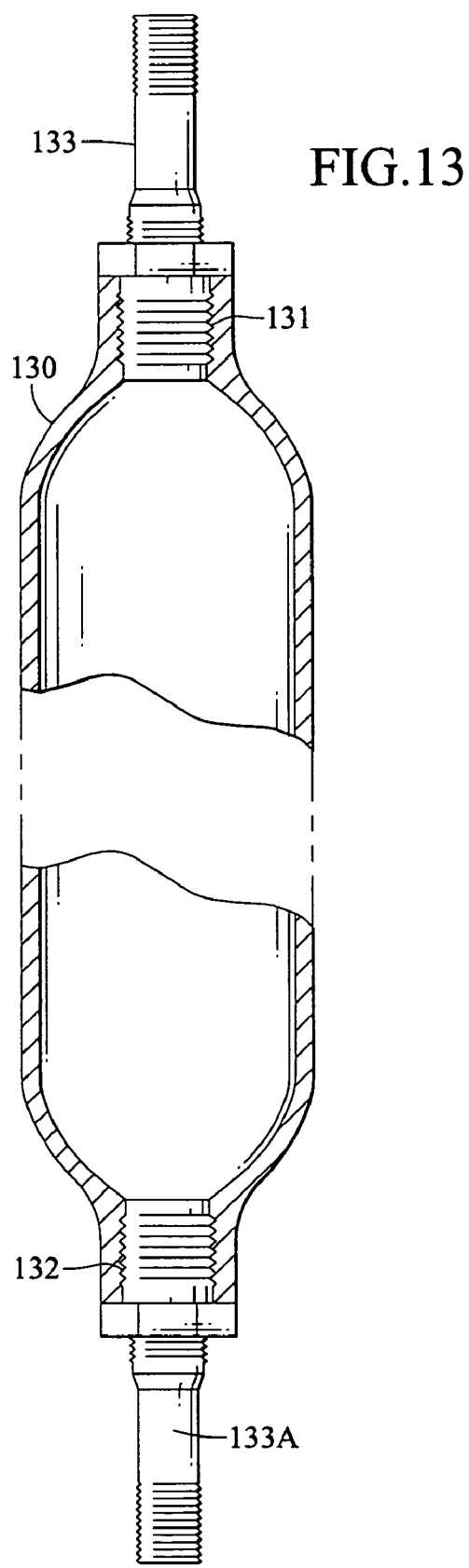
FIG. 13 is a cross sectional view of an alternative embodiment of a sample container.
Figure 14:
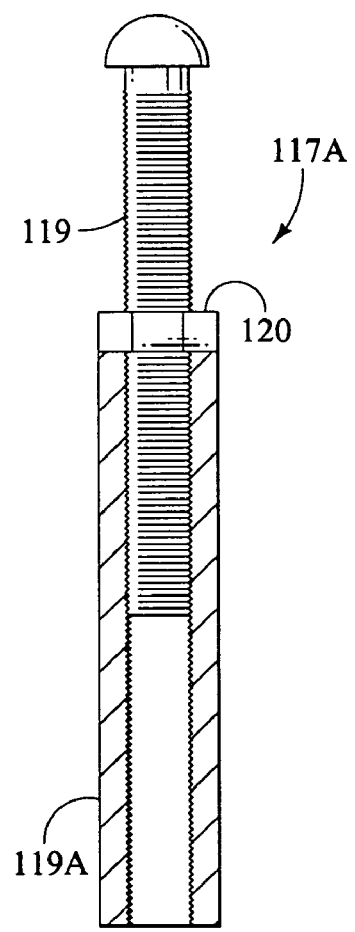
FIG. 14 is a cross sectional view of an extension rod pressurizer.

Prior to removing a sample from the sample container, it may be necessary to pressurize the sample. This may be accomplished by removing the cap retaining nut such as cap retaining nut 113A and then threadedly mounting extension rod pressurizer 117A as seen in FIG. 14, to an end cap valve assembly such as first self sealing valve 76. By using the extension rod pressurizer 117A to press first self sealing valve 76 further into the sample container, increased pressure of the sample may be obtained. Extension rod pressurizer 117A is composed of an internally threaded tube 119A which is disposed over the externally threaded end of the first self sealing valve 76. Bolt 119 is threaded into internally threaded tube 119A and held by lock nut 120. The length of the extension rod pressurizer may be adjusted by loosening the lock nut 120 and threading bolt 119 farther into or out of threaded tube 119A. Another form of sample container is illustrated in FIG. 13. Sample container 130 has a first internally threaded end 131 and a second internally threaded end 132. An first externally threaded end valve 133 with the same internal mechanism of first self sealing valve 76 may then be inserted into first internally threaded end 131 and a second externally threaded end valve 133A may be inserted into a second internally threaded end 132 thus creating a sample container.

Figure 5:
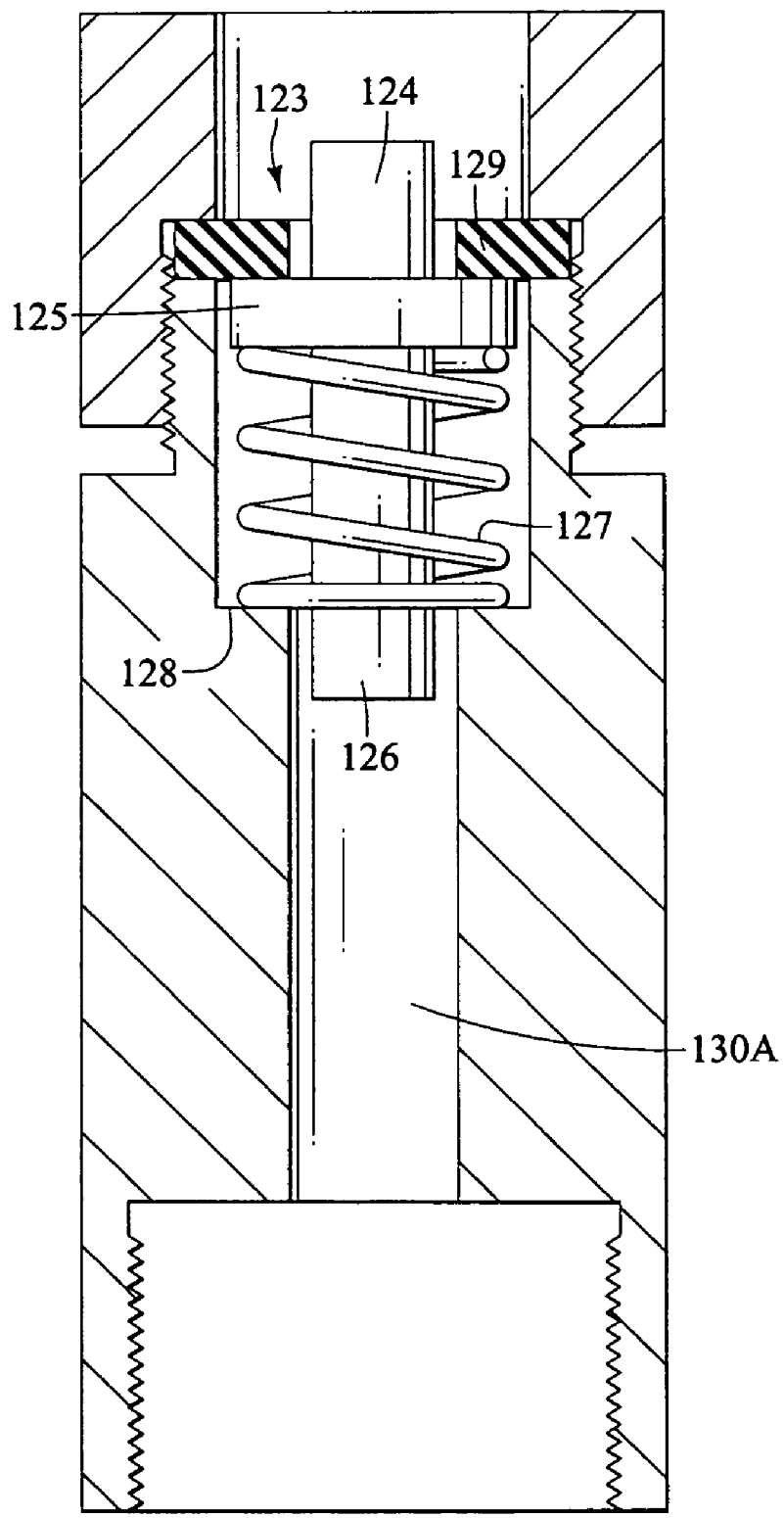
FIG. 5 is a cross sectional view of a self-sealing chuck.

An alternative mode of configuration for the fixed chuck and chuck heads of the spring loaded chuck is seen in FIG. 5. Here, the plunger depressor 123 in addition to a finger member 124 and a transverse member 125, has a stem member 126. Spring 127 rests between seat 128 and transverse member 125. The tension in spring 127 creates a seal between transverse member 125 and seal 129. This configuration allows any fluid or gas trapped in central bore 130 to remain captured. This is especially important when noxious gas for fluid is being sampled with this system.

DETAILED DESCRIPTION OF THE INVENTION

FIG. 1. illustrates the major components of the gas sampling apparatus. The gas sampling apparatus is given structure by its frame 1. The frame is composed of a rigid substance, usually metal, and exhibits a longitudinal planar segment 40. The frame is further composed of a first planar segment end 41 and a second planar segment end 42. A first panel 43 emanates from the first planar segment end 41 and is oriented at right angles to the planar segment 40. The first panel 43 exhibits a plurality of apertures first panel first aperture 44A, first panel second aperture 44B and first panel third aperture 44C. A second panel 45 emanates from the second planar segment end 42 again at right angles to the planar segment 40. The second panel 45 also exhibits a plurality of apertures, second panel first aperture 46A, second panel second aperture 46B and second panel third aperture 46C, in this case three in number, that correspond to and are opposite the apertures 44A, 44B, and 44C, exhibited by first panel 43. Mounted to first panel 43 and through the outermost apertures 44A and 44C of first panel 43 are first fixed chuck 4 and second fixed chuck 13. Mounted to second panel 45 and within the outermost apertures 46A and 46C are first spring-loaded chuck 6 and second spring loaded chuck 11.

First spring-loaded chuck 6 and second spring-loaded chuck 11 as well as first fixed chuck 4 and second fixed chuck 13 their associated flexible connectors and the frame provide the mounting apparatus for first sample container 5 and the substantially similar, second sample container 12. Turning for a moment to FIG. 8, it is seen that the first sample container 5 is composed of a first annular chamber 72 exhibiting a first annular chamber end 74 and a second annular chamber end 73. FIG. 9 shows that first annular chamber end 74 exhibits first swaged edge 106 with first opposite notch 107A and second opposite notch 107B. Turning to FIG. 16, and alternative means of swaging the edge is seen. Here the edge is swaged in a plurality of small increments or dimples, first swage 121A, second swage 121B, third swage 121C, and fourth swage 121D, around the edge's diameter. This can facilitate the insertion of other forms of end cap valves. Turning now to FIG. 8, the first swaged edge 106 of first samples container 5 is shown disposed within the first end cap central bore 75A of first end cap 75. Disposed through both first annular chamber end central aperture 109A and first end cap central aperture 109 is first self-sealing value 76. The end caps and nuts fixing the end caps to the self-sealing valves constitute the self-sealing valve.

Turning now to FIG. 15, the first end cap valve body 77 is illustrated which is one of the components of the first end cap valve assembly 76. It is composed of a transverse base 78 and annular section 79. Annular section 79 exhibits first annular section end 80 and second externally threaded annular section end 81, which is attached to the transverse base 78. Valve body central bore 110 extends through both transverse base 78 and the annular section 79. The first annular section end 80 exhibits both external threads 80B and internal thread 80A within the valve body central bore 110. The valve body central bore 110 exhibits a conical narrowing that comprises the central bore valve seat section 82. It is here that a first plunger-activated valve 86 as seen in FIG. 12, is seated. Turning now to FIG. 12, plunger activated valve 86 is shown. First plunger activated valve 86 is composed of a valve body 86A having a central cavity 90. Externally threaded first plunger valve body end 91 has a central bore 92 and a plurality of apertures, first valve body aperture 93A and second valve body aperture 93B that communicate with the central cavity 90. The second plunger valve body end 94 also exhibits a corresponding central bore 95 with an annular space 102 also communicating with the central cavity 90. The exterior of the valve body 86 exhibits a conical plunger valve body segment 105. A plunger valve body gasket 114 is seated around the conical plunger valve body segment 105 and substantially corresponds to the shape of the central bore valve seat section 82 shown in FIG. 15. Within the central cavity 90, first plunger rod support 96 has a central bore 97 and a plurality of plunger rod support apertures, first plunger rod support aperture 98A and second plunger rod support aperture 98B. The first plunger rod support is fixed to the interior walls of the central cavity 90. A second plunger rod support 99 also has a central bore 92 and a plurality of apertures second plunger rod support first aperture 101A and second plunger rod support second aperture 101B. The second plunger rod support 99 is also fixed to the interior walls of the central cavity 90. Thus, the central bores of the second plunger valve body end 94, the second plunger rod support 99, the first plunger rod support 96 and the first plunger valve body end 91 all correspond such that plunger 87 can be disposed through all. Plunger 87 has a first plunger end 103 disposed outside central cavity 90 and above valve body 86A. First plunger end 103 also exhibits a cap 103A that acts as a stop and prevents first plunger end 103 from fully entering valve body 86A. A second plunger end 104 is also disposed outside the central cavity 90 and below valve body 86. Second plunger end 104 exhibits cap 104A which prevents the second plunger end 104 from fully entering valve body 86A and also provides an air tight seal against plunger gasket 88. Plunger 87 also exhibits spring stop 115 fixed to plunger 87 between first plunger rod support 96 and second plunger rod support 99 but at a point on plunger 87 where the spring stop 115 cinnybucates with the interior surface 96A of the first plunger rod support 99. Fixed to the second plunger end 94 in such a manner as to preclude leakage around the plunger 87 is plunger gasket 88. Plunger gasket 88 seals the central bore 92 and annular space 102 of second plunger valve body end 94 by being held against the second plunger valve body end 94 by the pressure exerted by spring 89 on spring stop 115. Now returning to FIG. 15, it can be seen that when second plunger valve body end 94 of plunger activated valve 86 is inserted into first annular section end 80 of first end cap valve body 77, externally threaded first plunger valve body end 91 may be disposed and threadedly mounted within the internal threads 80A of first annular section end 80. Disposition of plunger activated valve 86 is to such a depth as to press plunger valve body gasket 114 (FIG. 12) firmly against central bore valve seat section 82 creating a seal.

Turning again to FIG. 8, it is seen that an annular rubber ring 111 is disposed over the annular section 79 and seats on the transverse base 78. Washer 112 is likewise disposed over the annular section 79 and seats on the annular rubber ring 111. Nut 113 is then threaded down over the second externally threaded annular section end 81 seen in FIG. 15. Insertion of the components of the first end cap valve stem assembly is facilitated by first opposite notch 107A and second opposite notch 107B shown in FIG. 9. Once the first self-sealing valve 76 is within the first annular chamber 72, nut 113 is tightened thereby applying pressure to washer 112 which in turn applies pressure to and expands the annular rubber ring 111 such that full diameter contact with the walls of the first annular chamber 72 and a tight seal is achieved. The first end cap 75 is then disposed over the first annular chamber end 74. Cap retaining nut 113A is then disposed over annular section 79 and then threaded over second annular section end 81 until the nut communicates with the end cap exterior 108. The first self-sealing valve 76 is then drawn toward the first swaged edge 106 which now retains the end cap valve assembly within first annular chamber 72 and holds the end cap in place. The second end cap 83 and second self sealing valve 76A are similarly mounted within the second annular chamber end 73.

Now turning to FIG. 6, first fixed chuck 4 is illustrated. First fixed chuck 4 is composed of an annular body 61 with externally threaded end 63 and internally threaded end 62. A central bore exists between them. A first central bore section 64 is seen followed by larger diameter second central bore section 64A. The differences in diameters produce seat 66. Upon seat 66 rests plunger depressor 67. Plunger depressor 67 has two components, a first finger member 68 and a first transverse member 69. The first transverse member 69 is that portion of the plunger depressor 67 which communicates with the seat 66. A first flexible washer 71 is disposed over the first finger member 68, first finger member disposed within first flexible washer central bore 71A, such that first flexible washer 71 rests on externally threaded end 63. However, as show in FIG. 7, the first transverse member is not a disk but is rectangular in shape such that only a portion of first flexible washer 71 is in contact with first transverse member 69 thus allowing fluid or gas to flow through first flexible washer 71, past first transverse member 69 into air passage aperture 70 and then into first central bore section 61 and beyond. FIG. 6 shows a first plunger depressor retaining cap 116 which is disposed over the externally threaded end 63. It holds first flexible washer 71 in position and thereby retains plunger depressor 67. First plunger depressor retaining cap 116 exhibits a central bore 65 into which a first endcap valve assembly 76 or second endcap valve assembly 76A can be inserted. The second fixed chuck 13 is configured substantially similar to the first fixed chuck 4.

Configured similarly to the fixed chucks 4 and 13 is the first chuck head 117 of the first spring loaded chuck 6 and second spring loaded chuck 11 as shown in FIG. 10. Disposed within the internally threaded end of first chuck head 117 is first pipe 118 having first pipe first end 118A and first pipe second end 118B. First pipe 118 then extends through first bushing 121 with first pipe second end 118B threadedly attached to a first flexible connector fitting 7A of such a diameter as to prevent pipe 118 from being returned through bushing 121. Bushing 121 is fixed within an outer second panel aperture 46C of second panel 45 by snap ring 118C. Spring 118D is disposed over pipe 118 and rests between chuck head 117 and bushing 121. When chuck head 117 is depressed by sample container 5, pipe 118 slides downward through bushing 121. As chuck head 117 is depressed, the tension in spring 118D is increased allowing chuck head 117 to return upward after pressure is released. Second spring loaded chuck 11 is configured in a substantially similar fashion being mounted in the second panel first aperture 46A of panel 45.

It can be seen in FIG. 1 that to insert a sample container, for example, sample container 5, the second self-sealing valve 76A is disposed within the mouth of spring loaded chuck 6. Downward pressure is then applied whereupon first spring loaded chuck 6 is pressed down and through spring loaded chuck first bushing 121. Spring loaded chuck 6 is able to be depressed a sufficient distance to allow the upper end of sample container 5 to be positioned under fixed chuck 4. Downward pressure on the sample container is then released allowing the first self sealing valve 76 of sample container 5 to seat within fixed chuck 4. A similar procedure is utilized to mount the second sample container 12 between the second spring loaded chuck 11 and second fixed chuck 13.

At this point, it should be noted that the insertion of the end cap valve assemblies into spring loaded chuck 6 and fixed chuck 4 causes the ends of the end cap valve assemblies to be pressed into and to be pressed against the flexible washers such as the first flexible washer 71 as illustrated in FIG. 10. This produces a seal. A finger member such as first finger member 68 of plunger depressor 67 will come in contact with a plunger such as plunger 87 of plunger activated valve 86, (Seen in FIG. 12) causing the sample container, such as sample container 5 to open. This happens on both ends of the sample container allowing gas or fluid to pass through when the sample container is seated in the fixed and spring loaded chucks.

Returning to FIG. 1, first three-way valve 2 is mounted to panel 43 between first fixed chuck 4 and second fixed chuck 13. First fixed chuck 4 is connected to the first valve left outlet 48. The second fixed chuck 13 is connected to the first valve right outlet 49. Mounted so as to read pressure from the first valve inlet 47 is pressure gauge 150. A similar configuration is seen with the second three-way valve 8, which is similarly attached to second panel 45. The first spring loaded chuck 6 is connected to the second valve left inlet 55. Second spring loaded chuck 11 is further connected to second valve right inlet 56. Mounted to communicate and to read pressure from second valve outlet 54 is second pressure gauge 151. Since first spring loaded chuck first pipe 118 may be pressed through first spring loaded chuck first bushing 121, the first spring loaded chuck 6 is connected to second valve left inlet 55 by means of first flexible connector 7. Similarly, second spring loaded chuck 11 is connected to second valve right inlet 56 by means of second flexible connector 10. Valve control rod 9 extends through the second panel aperture 46B in second panel 45 and first panel aperture 44B in first panel 43. Thus control rod 9 communicates simultaneously with first three-way valve 2 and second three-way valve 8. Control handle 9C communicates with control rod 9 facilitating its rotation. The first three way valve, second threeway valve, control rod and control handle comprise the flow director.

Now turning to FIG. 2, we first see that control handle 9C is oriented toward first sample container 5. Control rod 9 exhibits first control rod end 9A and second control rod end 9B. First control handle end 9A is attached to and operates a first valve flow director 50 which is mounted internally in first three-way valve 2. The first valve flow director 50 exhibits a passage 51 with a first passage end 52 and a second passage end 53. When the control handle 9A is orientated toward sample container 5, first passage end 52 aligns with first valve inlet 47. Simultaneously, the second passage end 53 aligns with first valve left outlet 48. It can then be seen that gas may flow into the first valve inlet 47 through first valve flow directing means passage 51, out first valve left outlet 48, through second flexible connector 7C, then through first fixed chuck 4 into sample container 5. Control rod second end 9B is similarly connected to second valve flow directing means 57. The second valve flow directing means exhibits conduit 58 which provides the same function as passage 51 in first valve flow directing means 50. Conduit 58 exhibits a first conduit end 59 and second conduit end 60. Control rod 9 is attached to both the first valve flow directing means 50 and second valve flow directing means 57 such that when the first valve flow directing means 50 is oriented as described above, the second valve flow directing means 57 is oriented in such a way that first conduit end 59 communicates with second valve inlet 55 and second conduit end 60 communicates with second valve outlet 54. It can be seen that any gas or fluid in sample container 5 may then flow through second spring loaded chuck 6 through first flexible connector 7 into second valve left inlet 55 through second valve flow director conduit 58 and finally out second valve outlet 54. In this configuration, no gas will flow through first valve right outlet 49, through second sample container 12 or second valve right inlet 56. Now turning to FIG. 3, it can be seen that when control handle 9C is directed toward second sample container 12, the first valve flow directing means 50 is oriented such that first passage end 52 communicates with first valve inlet 47 and second passage end 53 is now oriented with first valve right outlet 49. Now it can be seen that gas may flow in first valve inlet 47 through first valve flow directing means passage 51 into the first valve right outlet 49 through fixed chuck 13 and into second sample container 12.

Again, when control handle 9C is oriented towards second sample container 12, the second valve flow directing means 57 has its conduit 58 oriented in such a way that first conduit end 59 communicates with second valve inlet 56 and second conduit end 60 communicates with second valve right outlet 54. Now it can be seen that fluid or gas in sample container 12 may flow through spring loaded chuck 11 then through second flexible connector 7B into second valve inlet 56 through conduit 58 and into second valve outlet 54.

A method of acquiring samples would be to allow gas to flow though sample container 5 and then after having mounted sample container 12, orienting the control handle so that gas now flows through sample container 12 and gas flow is terminated through sample container 5. In this way, sample container 5 may be removed from the system and an empty sample container mounted. When sufficient sample has been gathered within sample container 12, the control handle 9C would then again be moved toward the fresh sample container thus occluding gas flow through sample container 12 whereupon it may be removed from the system. By alternating the removal of full sample containers and the replacement with empty containers, continuous or periodic samples in a line of gas or fluid flow may be obtained.

What is claimed is:

1. A gas sampling apparatus comprising:
    sample containers which are two in number further comprising a first sample container and a second sample container into which gas samples are sequentially disposed, a mounting apparatus into which said sample containers are demountably disposed and fluidly connected, said second sample container is identical in construction to said first sample container,
    said first sample container further comprising a first sample container first end having a first edge wherein said first edge is partially curved inward around the circumference of said first sample container first end, said first edge having first opposing notches, first sample container second end having a second edge wherein said second edge is partially curved inward around the circumference of said first sample container second end said second edge having second opposing notches,
    a first self-sealing valve demountably and fluidly connected to said first sample container first end,
    a first self-sealing valve retainer demountably connected to said first self sealing valve and to said first sample container first end whereby said first self sealing valve is fixed and prevented from advancing within said first sample container,
    a second self-sealing valve demountably and fluidly connected to said first sample container second end,
    a second self-sealing valve retainer demountably connected to said second self sealing valve and to said first sample container second end whereby said second self sealing valve is fixed and prevented from advancing within said first sample container,
    said first self sealing valve, when said first self sealing valve retainer is removed, being capable of being advanced within said first sample container while maintaining a seal between said first self sealing valve and said first sample container, whereby said gas samples may be compressed,
    said second self sealing valve, when said second self sealing valve retainer is removed, being capable of being advanced while maintaining a seal between said second self sealing valve and said first sample container, within said first sample container whereby said gas samples may be compressed,
    a first annular ring sealably connected to said first self sealing valve, whereby said first annular ring produces a seal against the walls of said first sample container, said first annular ring and said first self sealing valve may be inserted through said first opposing notches and retained within said first sample container first end,
    a second annular ring sealably connected to said second self sealing valve, whereby said second annular ring produces a seal against the walls of said first sample container, said second annular ring and said second self sealing valve may be inserted through said second opposing notches and retained within said first sample container second end,
    a plurality of flow directors fluidly attached to said mounting apparatus, said plurality of flow directors sequentially disposing gas into said mounting apparatus and sample containers.

2. The gas sampling apparatus of claim 1 wherein said first edge of said first sample container first end further comprises a plurality of edge tabs wherein said edge tabs are partially curved inward.

3. The gas sampling apparatus of claim 1 wherein said second edge of said first sample container second end further comprises a plurality of edge tabs wherein said edge tabs are partially curved inward.

4. The gas sampling apparatus of claim 1 wherein said mounting apparatus further comprises
    a frame,
    a plurality of fixed chucks mounted to said frame, said plurality of fixed chucks further comprising a first fixed chuck and a second fixed chuck, a plurality of opposing spring loaded chucks mounted to said frame opposite said plurality of fixed chucks, said opposing spring loaded chucks capable of being compressed in length, allowing the distance between said opposing spring loaded chucks and said fixed chucks to be increased whereby said sample containers may be inserted therebetween, said plurality of opposing spring loaded chucks further comprising a first opposing spring loaded chuck and a second opposing spring loaded chuck, said opposing spring loaded chucks capable of being decompressed thereby retaining said sample containers between said fixed chucks and said opposing spring loaded chucks, whereby said sample containers are fluidly connected to said opposing spring loaded chucks and said fixed chucks, a plurality of flexible connectors.

5. The gas sampling apparatus of claim 4 wherein said flow directors further comprise:
   a first flow director,
   a second flow director,
   a plurality of flexible connectors fluidly connecting said fixed chucks to said first flow director,
   a plurality of flexible connectors fluidly connecting said opposing spring loaded chucks to said second flow director.

6. The gas sampling apparatus of claim 4 wherein said fixed chucks are self sealing.

7. The gas sampling apparatus of claim 4 wherein said opposing spring loaded chucks are self sealing.

8. The gas sampling apparatus of claim 5 wherein said plurality of flexible connectors further comprising:
   a first flexible connector fluidly connected to said first fixed chuck,
   a second flexible connector fluidly connected to said second fixed chuck,
   a third flexible connector fluidly connected to said first opposing spring loaded chuck,
   a fourth flexible connector fluidly connected to said second opposing spring loaded chuck.

9. The gas sampling apparatus of claim 4 wherein said frame further comprises:
   a longitudinal planar segment having a first planar segment end and a second planar segment end,
   a first panel attached to said first planar segment end,
   a second panel attached to a said second planar segment end,
   said first panel and said second panel attached at right angles to said longitudinal planar segment,
   said first and second panel having a plurality of opposing apertures.

10. The gas sampling apparatus of claim 9 wherein said first panel further comprises:
    a first panel first aperture,
    a first panel second aperture,
    a first panel third aperture,
    said second fixed chuck fixedly mounted within said first panel first aperture,
    said first fixed chuck fixedly mounted within said first panel third aperture.

11. The gas sampling apparatus of claim 9 wherein said second panel further comprises:
    a second panel first aperture,
    a second panel second aperture,
    a second panel third aperture,
    said second opposing spring loaded chuck fixedly mounted within said second panel first aperture, said first opposing spring loaded chuck fixedly mounted within said second panel third aperture.

* * * * *